US012179040B2

(12) United States Patent
Liu et al.

(10) Patent No.: US 12,179,040 B2
(45) Date of Patent: Dec. 31, 2024

(54) SYSTEMS AND METHODS FOR ADJUSTING BEAM-LIMITING DEVICES

(71) Applicant: SHANGHAI UNITED IMAGING HEALTHCARE CO., LTD., Shanghai (CN)

(72) Inventors: Yanfang Liu, Shanghai (CN); Yifeng Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 594 days.

(21) Appl. No.: 17/210,426

(22) Filed: Mar. 23, 2021

(65) Prior Publication Data

US 2021/0290979 A1    Sep. 23, 2021

(30) Foreign Application Priority Data

Mar. 23, 2020    (CN) .......................... 202010209464.9

(51) Int. Cl.
*A61B 5/00* (2006.01)
*A61N 5/10* (2006.01)

(52) U.S. Cl.
CPC ......... *A61N 5/1065* (2013.01); *A61N 5/1077* (2013.01)

(58) Field of Classification Search
CPC .......... A61N 2005/1095; A61N 5/1065; A61N 5/1077
See application file for complete search history.

(56) References Cited

U.S. PATENT DOCUMENTS

| 4,754,147 | A | 6/1988 | Maughan et al. |
| 6,314,159 | B1 | 11/2001 | Siochi |
| 7,221,733 | B1 | 5/2007 | Takai et al. |
| 2001/0036017 | A1 | 11/2001 | Brown et al. |
| 2001/0043669 | A1 | 11/2001 | Ein-Gal |
| 2003/0081721 | A1 | 5/2003 | Siochi |

(Continued)

FOREIGN PATENT DOCUMENTS

| CN | 2376318 Y | 5/2000 |
| CN | 101757737 A | 6/2010 |

(Continued)

OTHER PUBLICATIONS

First Office Action in Chinese Application No. 202010209464.9 mailed on Apr. 30, 2021, 20 pages.

*Primary Examiner* — Mark D Remaly
(74) *Attorney, Agent, or Firm* — METIS IP LLC

(57) ABSTRACT

Systems and methods for adjusting a beam-limiting device, the beam-limiting device including a plurality of movable components for shaping a radiation beam. The methods may include for each of the plurality movable components, determining an initial location of the movable component; determining a target location of the movable component; and determining, based on the initial location and the target location, a moving route of the movable component. The methods may also include causing the plurality of movable components to move along their respective moving routes. During the movement of the plurality of movable components along their respective moving routes, the shape of an irradiation region of the radiation beam passing through the beam-limiting device may remain unchanged or substantially unchanged.

20 Claims, 8 Drawing Sheets

(56) References Cited

U.S. PATENT DOCUMENTS

| | | |
|---|---|---|
| 2005/0145804 A1 | 7/2005 | Yanagisawa et al. |
| 2005/0152499 A1 | 7/2005 | Zhao et al. |
| 2010/0054408 A1 | 3/2010 | Echner |
| 2010/0166150 A1 | 7/2010 | Perkins et al. |
| 2012/0056098 A1 | 3/2012 | Harada |
| 2014/0235919 A1 | 8/2014 | Iwata |
| 2014/0270069 A1 | 9/2014 | Ganguly |
| 2015/0162107 A1 | 6/2015 | Kato et al. |
| 2015/0297158 A1 | 10/2015 | Bothorel et al. |
| 2017/0087387 A1 | 3/2017 | Nord et al. |
| 2017/0225015 A1 | 8/2017 | Thieme et al. |
| 2019/0175944 A1 | 6/2019 | Towe et al. |
| 2020/0043624 A1 | 2/2020 | Schnarr et al. |
| 2020/0061390 A1* | 2/2020 | Ma .................. A61N 5/1048 |

FOREIGN PATENT DOCUMENTS

| | | |
|---|---|---|
| CN | 204143885 | 2/2015 |
| CN | 107149727 A | 9/2017 |
| CN | 209734776 U | 12/2019 |
| EP | 2835149 B1 | 11/2017 |
| JP | H1128252 A | 2/1999 |
| JP | H11244401 A | 9/1999 |
| JP | 2016083351 A | 5/2016 |
| JP | 2018099247 A | 6/2018 |

\* cited by examiner

SYSTEMS AND METHODS FOR ADJUSTING BEAM-LIMITING DEVICES

CROSS-REFERENCE TO RELATED APPLICATIONS

This application claims priority of Chinese Patent Application No. 202010209464.9, field on Mar. 23, 2020, the contents of which are hereby incorporated by reference.

TECHNICAL FIELD

The disclosure generally relates to the field of medical devices, and more particularly relates to systems and methods for adjusting a beam-limiting device of a medical device.

BACKGROUND

Radiotherapy is widely used for disease treatment (e.g., cancer treatment). During a radiotherapy treatment, a beam-limiting device may be used to form a radiation field such that the radiation beam can reach a planning region (e.g., a lesion) of a patient through the radiation field of the beam-limiting device, which can avoid the radiation beam from irradiating healthy regions of the patient. The height of the beam-limiting device and locations of movable components (e.g., leaves) of the beam-limiting device may have an impact on the delivery efficiency and/or accuracy of the radiotherapy treatment. Therefore, it is desirable to provide systems and methods for adjusting/controlling a beam-limiting device, thereby improving the treatment efficiency and/or accuracy.

SUMMARY

In an aspect of the present disclosure, a system for adjusting a beam-limiting device, the beam-limiting device including a plurality of movable components for shaping a radiation beam is provided. The system may include at least one storage device including a set of instructions and at least one processor configured to communicate with the at least one storage device. When executing the set of instructions, the at least one processor may be configured to direct the system to perform following operations. The operations may include for each of the plurality movable components, determining an initial location of the movable component; determining a target location of the movable component; and determining, based on the initial location and the target location, a moving route of the movable component. The operations may also include causing the plurality of movable components to move along their respective moving routes. During the movement of the plurality of movable components along their respective moving routes, the shape of an irradiation region of the radiation beam passing through the beam-limiting device may remain unchanged or substantially unchanged.

In some embodiments, the radiation beam may include a center axis. for each of the plurality of movable components, its initial location may include a first initial location along the center axis and a second initial location on a plane perpendicular to the center axis, and its target location may include a third location along the center axis and a fourth location on the plane.

In some embodiments, for each of the plurality of movable components, the determining a target location of the movable component may include determining a region of interest (ROI) planned to be radiated; and determining the target location of each of the plurality of movable components based on the ROI and the initial locations of the plurality of movable components such that during the movement of the plurality of movable components, the irradiation region may be the same or substantially the same as the ROI.

In some embodiments, the target location of each of the plurality of movable components may be determined according to a principle of similar triangles.

In some embodiments, the beam-limiting device may be mounted on a gantry of a radiotherapy device. The initial location and the target location of each of the plurality of movable components may correspond to a first gantry angle. During the movement of the plurality of movable components, the gantry may remain at the first gantry angle.

In some embodiments, the at least one processor may be further configured to direct the system to perform the following operations. The operations may include causing the gantry to rotate from the first gantry angle to a second gantry angle. The operations may also include for each of the plurality movable components, determining a second initial location and a second target location of the movable component corresponding to the second gantry angle; and determining, based on the second initial location and the second target location, a second moving route of the movable component. The operations may further include causing the plurality of movable components to move along their respective second moving routes. During the movement of the plurality of movable components along their respective second moving routes, the shape of a second irradiation region of the radiation beam passing through the beam-limiting device may remain unchanged or substantially unchanged, and the gantry may remain at the second gantry angle.

In some embodiments, the beam-limiting device may include a multi-leaf collimator, and the plurality of movable components may include a plurality of leaves of the multi-leaf collimator.

In some embodiments, the radiation beam may include at least one of a radioactive beam, a photon beam, or an electron beam.

In some embodiments, when the plurality of movable components are at their respective initial locations, the beam-limiting device may have a first resolution. When the plurality of movable components are at their respective target locations, the beam-limiting device may have a second resolution that is greater than the first resolution.

In some embodiments, during the movement of the plurality of movable components along their respective moving routes, the size of an irradiation region of the radiation beam passing through the beam-limiting device may remain unchanged or substantially unchanged.

In some embodiments, the irradiation region may be formed by one or more actuated movable components of the plurality of movable components, and during the movement of the plurality of movable components along their respective moving routes, a count of the one or more actuated movable components increases.

In another aspect of the present disclosure, a method for adjusting a beam-limiting device is provided. The method may be implemented on a computing device including at least one processor and at least one storage device. The method may include for each of the plurality movable components, determining an initial location of the movable component; determining a target location of the movable component; and determining, based on the initial location and the target location, a moving route of the movable component. The method may also include causing the plurality of movable components to move along their respective moving routes. During the movement of the plurality of movable components along their respective moving routes, the shape of an irradiation region of the radiation beam passing through the beam-limiting device may remain unchanged or substantially unchanged.

In some embodiments, the radiation beam may include a center axis. For each of the plurality of movable components, its initial location may include a first initial location along the center axis and a second initial location on a plane perpendicular to the center axis, and its target location may include a third location along the center axis and a fourth location on the plane.

In some embodiments, for each of the plurality of movable components, the determining a target location of the movable component may include determining a region of interest (ROI) planned to be radiated; and determining the target location of each of the plurality of movable components based on the ROI and the initial locations of the plurality of movable components such that during the movement of the plurality of movable components, the irradiation region may be the same or substantially the same as the ROI.

In some embodiments, the target location of each of the plurality of movable components may be determined according to a principle of similar triangles.

In some embodiments, the beam-limiting device may be mounted on a gantry of a radiotherapy device. The initial location and the target location of each of the plurality of movable components may correspond to a first gantry angle. During the movement of the plurality of movable components, the gantry may remain at the first gantry angle.

In some embodiments, the method may further include causing the gantry to rotate from the first gantry angle to a second gantry angle. The method may also include for each of the plurality movable components, determining a second initial location and a second target location of the movable component corresponding to the second gantry angle; and determining, based on the second initial location and the second target location, a second moving route of the movable component. The method may also include causing the plurality of movable components to move along their respective second moving routes. During the movement of the plurality of movable components along their respective second moving routes, the shape of a second irradiation region of the radiation beam passing through the beam-limiting device may remain unchanged or substantially unchanged, and the gantry may remain at the second gantry angle.

In some embodiments, the beam-limiting device may include a multi-leaf collimator, and the plurality of movable components may include a plurality of leaves of the multi-leaf collimator.

In some embodiments, the radiation beam may include at least one of a radioactive beam, a photon beam, or an electron beam.

In some embodiments, when the plurality of movable components are at their respective initial locations, the beam-limiting device may have a first resolution. When the plurality of movable components are at their respective target locations, the beam-limiting device may have a second resolution that is greater than the first resolution.

In some embodiments, during the movement of the plurality of movable components along their respective moving routes, the size of an irradiation region of the radiation beam passing through the beam-limiting device may remain unchanged or substantially unchanged.

In some embodiments, the irradiation region may be formed by one or more actuated movable components of the plurality of movable components, and during the movement of the plurality of movable components along their respective moving routes, a count of the one or more actuated movable components increases.

In another aspect of the present disclosure, a non-transitory computer readable medium is provided. The medium may include executable instructions that, when executed by at least one processor, direct the at least one processor to perform a method for adjusting a beam-limiting device, the beam-limiting device including a plurality of movable components for shaping a radiation beam. The method may include for each of the plurality movable components, determining an initial location of the movable component; determining a target location of the movable component; and determining, based on the initial location and the target location, a moving route of the movable component. The method may also include causing the plurality of movable components to move along their respective moving routes. During the movement of the plurality of movable components along their respective moving routes, the shape of an irradiation region of the radiation beam passing through the beam-limiting device may remain unchanged or substantially unchanged.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
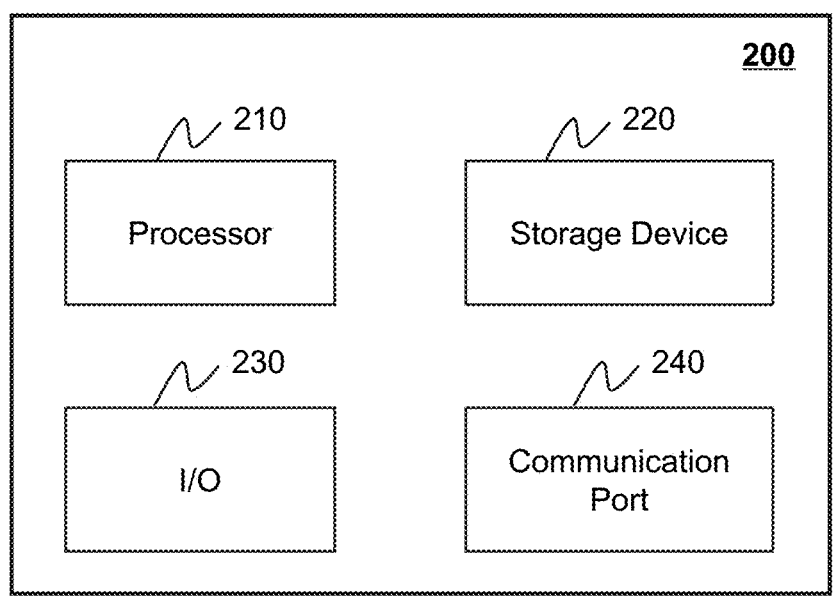
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image. The subject may include a biological subject (e.g., a human, an animal), a non-biological subject (e.g., a phantom), etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for medical diagnosis and/or treatment. In some embodiments, the systems for diagnosis and/or treatment may include a radiotherapy system (e.g., a photon therapy system, an electronic therapy system, a proton therapy system, etc.). The photon therapy system may be configured to treat a subject using a photon beam (e.g., radioactive rays, such as X rays, γ rays, etc.). The electron therapy system may be configured to treat the subject using an electron beam. The proton therapy system may be configured to treat the subject using a proton beam. For example, radioactive rays may be used to irradiate a region of interest (e.g., a tumor region) of a patient for cancer treatment. The region of interest (ROI) of a patient may refer to a ROI planned to be radiated. For brevity, the ROI planned to be radiated may also referred to as a planning region in the present disclosure. As another example, photon beams or electron beams can be used to irradiate a skin surface region of a patient for removing freckles. In some embodiments, photon beams, electron beams, and protons beams may also be referred to as radiation beams for brevity. The radiation beams may need to pass through a beam-limiting device which can shape the radiation beams to reach the planning region of the subject. For illustration purposes, the present disclosure is provided with a radiotherapy system using radioactive rays as an exemplary scenario in the following description, which is not intended to limit the scope of the present disclosure. The system and method for control/adjusting the beam-limiting device disclosed in the present disclosure may also be applied to any treatment or diagnostic system (e.g., a photon therapy system, an electron therapy system, a proton therapy system) that needs beam shape constraints.

An aspect of the present disclosure relates to systems and methods for adjusting a beam-limiting device. The beam-limiting device may include a plurality of movable components for shaping a radiation beam. For each of the plurality movable components, the systems and methods may determine an initial location of the movable component, and determine a target location of the movable component. For each of the movable components, the systems and methods may further determine a moving route of the movable component based on the initial location and the target location of the movable component. The systems and methods may further cause the plurality of movable components to move along their respective moving routes. During the movement of the plurality of movable components along their respective moving routes, the shape of an irradiation region of the radiation beam passing through the beam-limiting device may remain unchanged or substantially unchanged.

According to some embodiments of the present disclosure, each movable component of the beam-limiting device may move along a first direction (which is parallel to a central axis of the radiation beam) and in a first plane (which is vertical to the central axis) simultaneously, which can improve the moving efficiency of the beam-limiting device. During the movement of the movable components of the beam-limiting device, the shape of an irradiation region of the radiation beam passing through the beam-limiting device may remain unchanged or substantially unchanged and match the shape of a planning region of the subject. In such cases, a treatment plan of the subject may not need to be adjusted even if the beam-limiting device moves. For example, the radiation duration and/or the radiation intensity may not need to be adjusted, thereby improving the treatment efficiency. Further, in some embodiments, during the movement of the movable components of the beam-limiting device from their initial locations to their target locations, the beam-limiting device may be closer to the subject, which may improve the conformity and resolution of the beam-limiting device.

Figure 1:
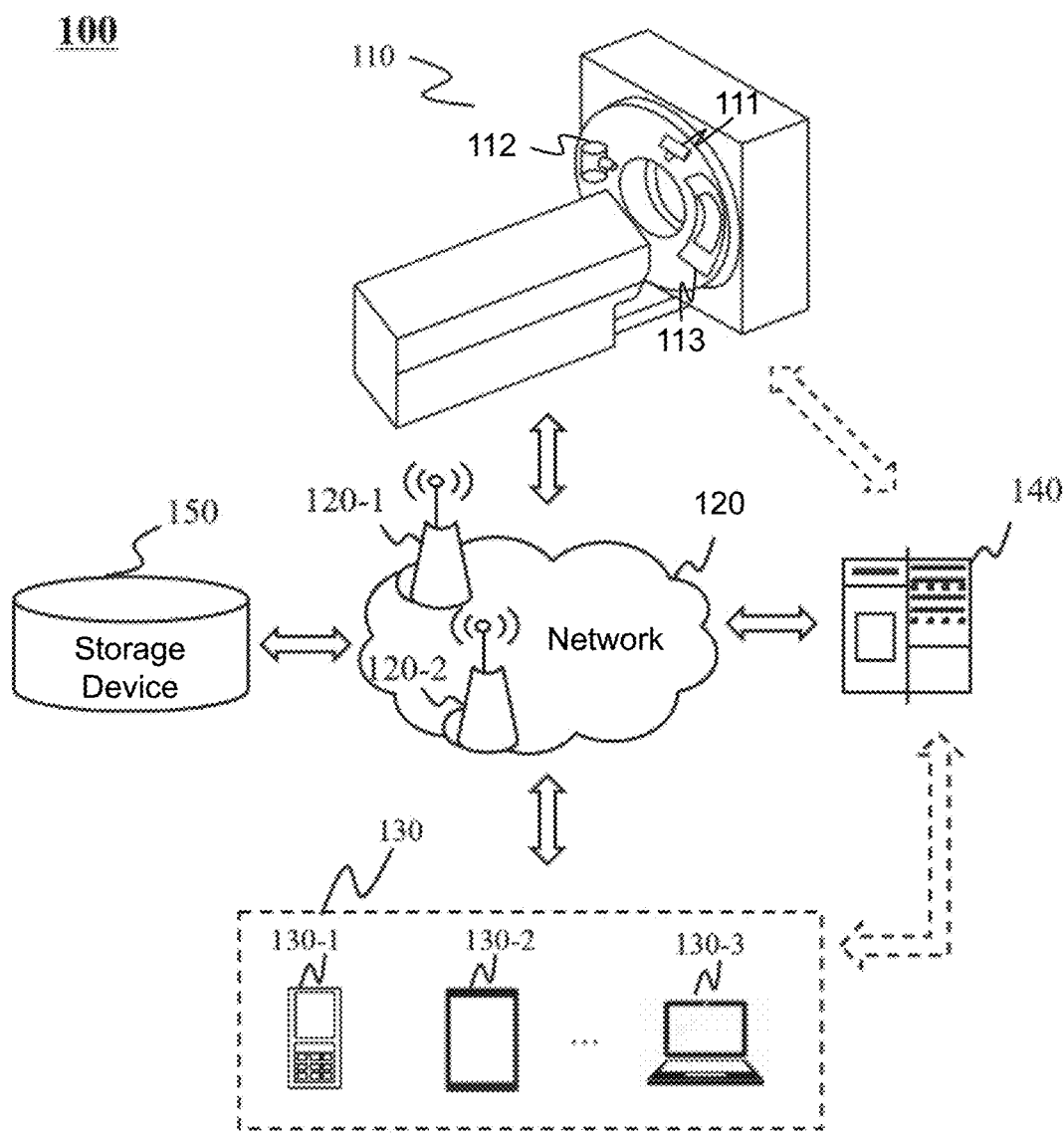
FIG. 1 is a schematic diagram illustrating an exemplary radiotherapy system according to some embodiments of the present disclosure.

FIG. 1 is a schematic diagram illustrating an exemplary radiotherapy system 100 according to some embodiments of the present disclosure. In some embodiments, the radiotherapy system 100 may include a conformal radiation therapy device, an image guided radiation therapy (IGRT) system, an intensity modulated radiation therapy (IMRT) device, an intensity modulated arc therapy (IMAT) device, or the like. Merely by way of example, an IGRT system may include a computed tomography (CT) guided RT system, a magnetic resonance imaging (MRI) guided RT system, an emission computer tomography (ECT) guided RT system (e.g., a single photon emission computed tomography (SPECT) guided RT system, a positron emission tomography (PET) guided RT system), an ultrasound guided RT system, a fluoroscopy imaging guided RT system, an X-ray imaging guided RT system, etc.

As shown in FIG. 1, the radiotherapy system 100 may include a radiotherapy device 110, a network 120, a terminal device 130, a processing device 140, and a storage device 150. The components of the radiotherapy system 100 may be connected in one or more of various ways. Mere by way of example, as illustrated in FIG. 1, the radiotherapy device 110 may be connected to the processing device 140 through the network 120. As another example, the radiotherapy device 110 may be connected to the processing device 140 directly (as indicated by the bi-directional arrow in dotted lines linking the radiotherapy device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The radiotherapy device 110 may be configured to perform radiotherapy on at least part of a subject. In some embodiments, the subject may include a biological subject (e.g., a patient) or a non-biological subject (e.g., a phantom). For example, the subject may include a specific part, organ, and/or tissue of a patient. As another example, the subject may include the head, the brain, the neck, the breast, the heart, the stomach, blood vessels, soft tissues, or the like, or any combination thereof. As still another example, the subject may include a region of interest (ROI), such as a tumor or a nodule of a patient. The term "object" or "subject" are used interchangeably in the present disclosure.

In some embodiments, the radiotherapy device 110 may include a single modality device. For example, the radiotherapy device 110 may include an X-ray therapy device, a Co-60 remote therapy device, a medical electron accelerator, etc. Alternatively, the radiotherapy apparatus 110 may include a multi-modality device (e.g., a double-modality device). The multi-modality device may be used to acquire image data of the subject and treat the subject. For example, the radiotherapy device 110 may include an IGRT device, such as a CT guided RT device, an MRI guided RT device, an ECT guided RT device, an ultrasound imaging guided RT device, a fluoroscopy imaging guided RT device, an X-ray imaging guided RT device, etc. For illustration purposes, the radiotherapy device 110 illustrated in FIG. 1 is provided with reference to a CT guided RT system, which is not intended to limit the scope of the present disclosure.

In some embodiments, the radiotherapy device 110 may include a treatment component, such as a treatment head 111. The treatment head 111 may be mechanically connected to a gantry. For example, the treatment head 111 may be mounted on the gantry, such that the treatment head 111 may rotate with the gantry. In some embodiments, the treatment head 111 may include a treatment radiation source, a beam-limiting device (also referred to as a beam-defining device), etc. The treatment radiation source may be configured to generate and emit a radiation beam toward the subject for treatment. The beam-limiting device may be configured to control and/or define the shape of the radiation beam generated by the radiation source.

In some embodiments, the beam-limiting device may include a collimator (e.g., a multi-leaf collimator (MLC)), a jaw, a cone, an aperture diaphragm, an extension cylinder, or any other component that can limit the transmission of a radiation beam, or any combination thereof. In some embodiments, the beam-limiting device may have a radiation field. The radiation beam may pass through the radiation field of the beam-limiting device and be shaped by the radiation field of the beam-limiting device. In some embodiments, the beam-limiting device may include one or more movable components arranged on a same end surface to form the radiation field of the beam-limiting device. Taking the MLC as an example, the MLC may include multiple leaves, which can be moved to different locations on an end surface to form different radiation fields of the MLC.

In some embodiments, the movable component(s) of the beam-limiting device may move along a height direction of the beam-limiting device to adjust the distance between the beam-limiting device and the subject. The height direction may also be referred to as a first direction. For example, the height direction may be parallel to a central axis of the radiation beam. Additionally or alternatively, the movable component(s) of the beam-limiting device may move in the end surface to adjust the radiation field of the beam-limiting device. The end surface on which the one or more movable components are arranged may also be referred to as a first plane. The first plane may be perpendicular to the central axis. Each of the movable component(s) of the beam-limiting device may move along a second direction in the first plane (e.g., any direction in the first plane). The second direction may be perpendicular to the first direction. In some embodiments, the beam-limiting device (e.g., the multiple leaves of the MLC) may be driven by one or more driving components (e.g., motors) to move along the first direction and/or the second direction in the first plane, such that the beam-limiting device may move to a specific location to adjust the shape of the radiation field of the beam-limiting device. More descriptions regarding the beam-limiting device may be found elsewhere in the present disclosure (e.g., FIG. 4 and the description thereof).

In some embodiments, the radiotherapy device 110 may include a treatment auxiliary component, such as an electronic field imaging device (EPID). The EPID may be configured to acquire image data relating to the subject before, during, and/or after each treatment session of the subject, e.g., for positioning the subject. In some embodiments, the EPID may include a detector configured to detect the radiation beam (e.g., X rays, γ rays, etc.) emitted from an imaging radiation source. In some embodiments, the treatment radiation source may be used as the imaging radiation source. Alternatively, the imaging radiation source may be different from the treatment radiation source. In some embodiments, the detector of the EPID may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

In some embodiments, the radiotherapy device 110 may include an imaging component, such as a CT device, an ultrasound imaging device, a fluoroscopy imaging device, an MRI device, a SPECT device, a PET device, an X-ray imaging device, or the like, or any combination thereof. Taking the CT device as an example, the CT device may include a cone beam computed tomography (CBCT) device that can perform a CBCT scan on the subject by emitting a cone beam toward the subject. As another example, the CT device may include a multi-slice spiral computed tomography (MSCT) that can perform an MSCT scan on the subject. As still another example, the CT device may include a comprehensive CT device that can perform both a CBCT scan and an MSCT scan on the subject. In some embodiments, the imaging component may include an imaging radiation source 112, a detector 113, etc., for imaging.

In some embodiments, the imaging component may be spaced by a distance from the treatment component. For example, the imaging component may be mounted on a same gantry as the treatment component. As another example, the imaging component may be mounted in a gantry different from that where the treatment component is mounted. In some embodiments, the gantry of the imaging component and the gantry of the treatment component may share an axis of rotation. The subject may be positioned in different locations on a couch of the radiotherapy device 110 for imaging and treatment. In some embodiments, the imaging radiation source and the treatment radiation source may be integrated as one radiation source (denoted as SO) to image and/or treat the subject.

In some embodiments, the radiotherapy device 110 may include one or more driving components configured to drive the movement of the beam-limiting device. The one or more components may include one or more first driving components and/or one or more second driving components. The one or more first driving components may be configured to drive the beam-limiting device (e.g., the plurality of movable components) to move along the first direction. The one or more second driving components may be configured to drive the beam-limiting device (e.g., the plurality of movable components) to move in the first plane. In some embodiments, each of the one or more first driving components may include one or more first motors and a first movement transmission unit of each first motor. Each of the one or more second driving components may include one or more second motors and a second movement transmission unit of each second motor. A motor and its corresponding movement transmission unit (e.g., a first motor and its corresponding first movement transmission unit, or a second motor and its corresponding second movement transmission unit) may be configured to drive a single movable or more than one movable component.

Alternatively, each of the plurality of driving components may drive one or more movable components to move along the first direction and in the first plane simultaneously. For example, each driving component may include a third motor and a third movement transmission unit. The third motor and the third movement transmission unit may drive one or more movable components to move along a beam direction. In some embodiments, a motor (e.g., a first motor, a second motor, or a third motor) may include a linear motor or a rotary motor. When the motor is a linear motor, its corresponding movement transmission unit (e.g., a first movement transmission unit, a second movement transmission unit, or a third movement transmission unit) may include a gear unit, a connecting rod unit, etc. When the motor is a rotary motor, its corresponding movement transmission unit (e.g., a first movement transmission unit, a second movement transmission unit, or a third movement transmission unit) may include a worm gear movement transmission unit, a ball screw movement transmission unit, a rack-pinion movement transmission unit, etc.

In some embodiments, the driving component(s) may receive an instruction from a control component (e.g., the processing device 140) and drive the beam-limiting device according to the instruction. For example, for a movable component, a first motor corresponding to the movable component may receive a first instruction to drive the movable component to move along the first direction, and a second motor corresponding to the movable component may receive a second instruction to drive the movable component to move in the first plane. The first motor and the second motor may drive the movable component to move along the first direction and in the first plane simultaneously based on the first and second instructions, respectively.

The network 120 may include any suitable network that can facilitate the exchange of information and/or data for the radiotherapy system 100. In some embodiments, one or more components (e.g., the radiotherapy device 110, the processing device 140, the storage device 150, the terminal device 130) of the radiotherapy system 100 may communicate information and/or data with one or more other components of the radiotherapy system 100 via the network 120.

For example, the processing device 140 may obtain a user instruction of a user (e.g., a doctor or an operator) or an initial location of the beam-limiting device from the terminal device 130 via the network 120. As another example, the processing device 140 may obtain a control instruction for controlling the movement of the beam-limiting device from the terminal device 130 via the network 120. In some embodiments, one or more components (e.g., the radiotherapy device 110, the processing device 140, the storage device 150, the terminal device 130) of the radiotherapy system 100 may communicate information and/or data with one or more external resources such as an external database of a third party, etc. The network 120 may be and/or include a public network (e.g., the Internet), a private network (e.g., a local area network (LAN), a wide area network (WAN))), a wired network (e.g., an Ethernet network), a wireless network (e.g., an 803.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points, such as base stations and/or internet exchange points, through which one or more components of the radiotherapy system 100 may be connected to the network 120 to exchange data and/or information.

The terminal device 130 may communicate and/or be connected with the radiotherapy device 110, the processing device 140, and/or the storage device 150. For example, the terminal device 130 may obtain a radiation dose that the subject receives during a treatment from the processing device 140. As another example, the terminal device 130 may obtain an image acquired by the EPID (also referred to as an EPID image) corresponding to the radiation dose that the subject receives. The terminal device 130 may send the EPID image to the processing device 140 for processing to determine the radiation dose that the subject receives. In some embodiments, the terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the smart mobile device may include a mobile phone, a personal digital assistant (PDA), a gaming device, a navigation device, a point of sale (POS) device, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 130 may be part of the processing device 140.

The processing device 140 may process data and/or information obtained from the radiotherapy device 110, the terminal device 130, and/or the storage device 150. For example, the processing device 140 may determine a set of target locations of the movable components of the beam-limiting device, e.g., based on a treatment plan of the subject. As another example, the processing device 140 may determine the treatment plan. As still another example, the processing device 140 may cause the plurality of movable components of the beam-limiting device to move to their respective target locations. For instance, the processing device 140 may send an instruction including a moving route of a movable component to a first motor corresponding to the movable component. The first motor may drive the movable component to move along the moving route based on the received instruction. The moving route may be defined by moving parameters, such as a moving distance along the first direction, a moving distance along the second direction in the first plane.

In some embodiments, the processing device 140 may include a single server or a server group. The server group may be centralized or distributed. In some embodiments, the processing device 140 may be local or remote. For example, the processing device 140 may access information and/or data stored in the radiotherapy device 110, the terminal device 130, and/or the storage device 150 via the network 120. As another example, the processing device 140 may be directly connected to the radiotherapy device 110, the terminal device 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 or a portion of the processing device 140 may be integrated into the radiotherapy device 110. In some embodiments, the processing device 140 may be implemented by a computing device 200 including one or more components as described in FIG. 2.

The storage device 150 may store data, instructions, and/or any other information. For example, the storage device 150 may store information relating to a treatment plan of the subject. In some embodiments, the storage device 150 may store data obtained from the radiotherapy device 110, the terminal device 130, and/or the processing device 140. In some embodiments, the storage device 150 may store data and/or instructions that the processing device 140 may execute or use to perform exemplary methods/systems described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the radiotherapy device 110, the processing device 140, the terminal device 130) of the radiotherapy system 100. One or more components of the radiotherapy system 100 may access the data or instructions stored in the storage device 150 via the network 120. In some embodiments, the storage device 150 may be directly connected to or communicate with one or more other components (e.g., the radiotherapy device 110, the processing device 140, the terminal device 130) of the radiotherapy system 100. In some embodiments, the storage device 150 may be part of the processing device 140.

In some embodiments, the radiotherapy system 100 may include a treatment planning system (TPS), which can determine a treatment plan of a subject that needs treatment. The treatment plan may describe how a radiotherapy treatment is planned to be performed on the subject, more specifically, how one or more radiation beams are delivered to a planning region (e.g., a tumor region) of the subject during each treatment session for treatment lasting a certain period, e.g., days. For example, the treatment plan may provide a total dose and a dose distribution in the planning region, movements of a beam-limiting device during each treatment session, etc. In some embodiments, the TPS may be part of the processing device 140.

It should be noted that the above description of the radiotherapy system 100 is merely provided for the purposes of illustration, and not intended to limit the scope of the present disclosure. For persons having ordinary skills in the art, multiple variations and modifications may be made under the teachings of the present disclosure. In some embodiments, the radiotherapy system 100 may include one or more additional components and/or one or more components of the radiotherapy system 100 described above may be omitted. Additionally or alternatively, two or more components of the radiotherapy system 100 may be integrated into a single component. A component of the radiotherapy system 100 may be implemented on two or more sub-components. In some embodiments, the storage device 120 may include a data storage device of a cloud computing platform, e.g., a private cloud, a public cloud, a hybrid cloud, a community cloud, etc. However, those variations and modifications also fall within the scope of the present disclosure.

FIG. 2 is a schematic diagram illustrating hardware and/or software components of an exemplary computing device according to some embodiments of the present disclosure. The computing device 200 may be used to implement any component of the radiotherapy system 100 as described herein. For example, the processing device 140 and/or the terminal device 130 may be implemented on the computing device 200, respectively, via its hardware, software program, firmware, or a combination thereof. Although only one such computing device is shown for convenience, the computer functions relating to the radiotherapy system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device 130 and/or the storage device 150. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the radiotherapy device 110, the terminal device 130, the storage device 150, or any other component of the radiotherapy system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 120) to facilitate data communications. The communication port 240 may establish connections between the processing device 140 and the radiotherapy device 110, the terminal device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
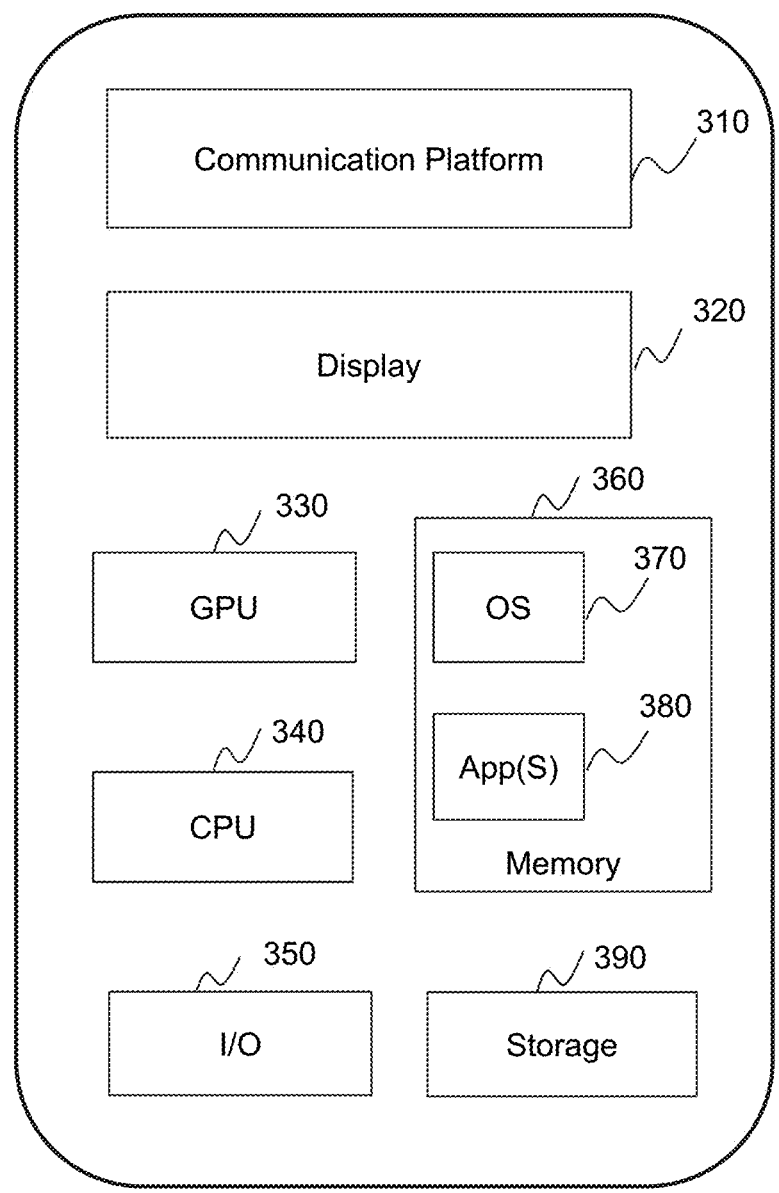
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, one or more components (e.g., a terminal device 130 and/or the processing device 140) of the radiotherapy system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiotherapy system via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
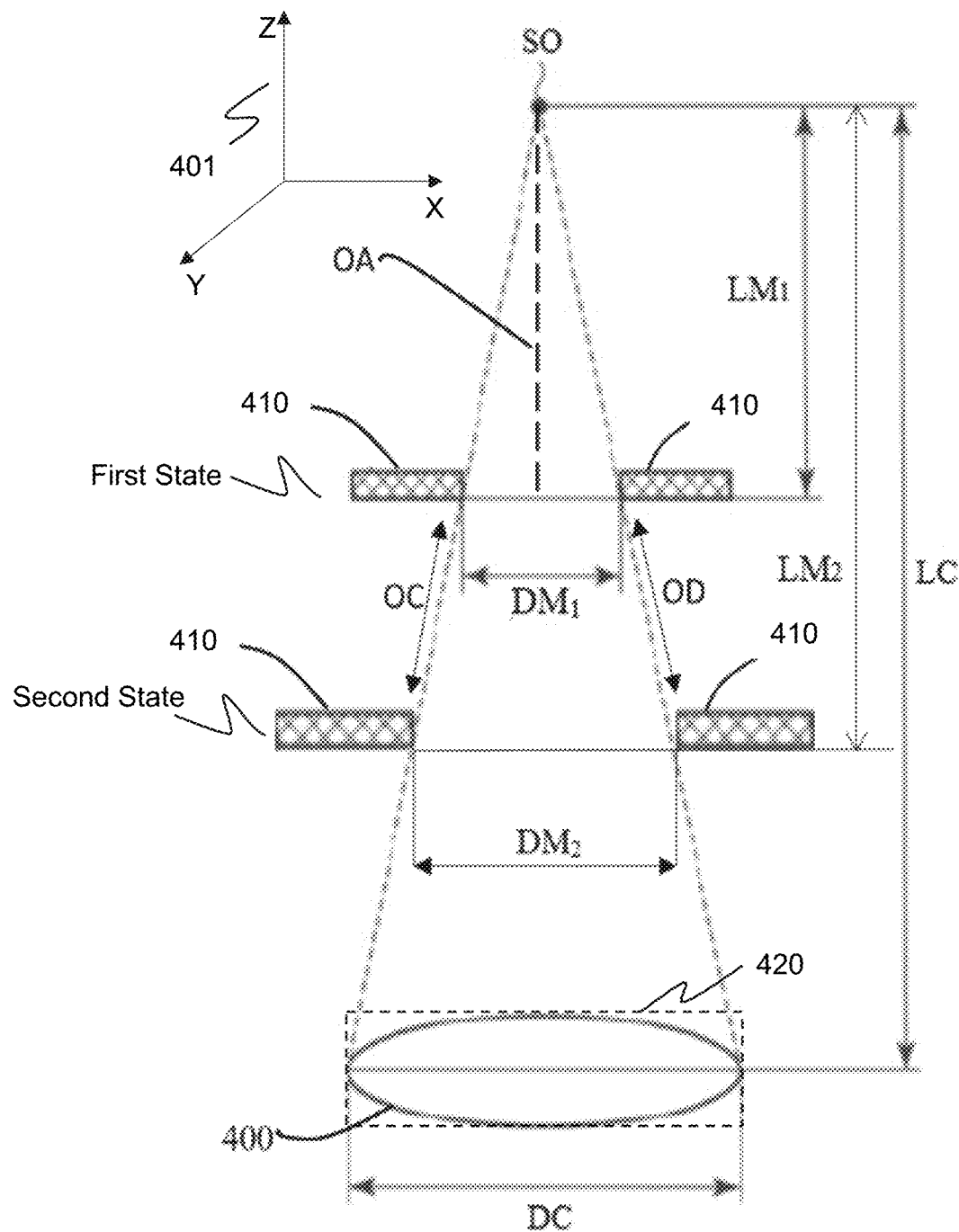
FIG. 4 is a schematic diagram illustrating exemplary states of a beam-limiting device according to some embodiments of the present disclosure

FIG. 4 is a schematic diagram illustrating exemplary states of a beam-limiting device according to some embodiments of the present disclosure. A shown in FIG. 4, when a radiation source SO is located at a specific gantry angle, a radiation beam emitted from the radiation source SO may pass through the beam-limiting device to irradiate a subject 400 for, e.g., treatment purposes. The radiation beam may include a photon beam, an electron beam, a proton beam, etc. Merely by way of example, the radiation beam may include radioactive rays (e.g., X rays, γ rays, etc.). The radiation source SO may include a main optical axis (denoted as OA in FIG. 4). As used herein, a main optical axis OA of a radiation source SO refers to a central axis of a radiation beam emitted from the radiation source SO. For brevity, a direction parallel to the main optical axis OA may be denoted as a first direction.

In some embodiments, a coordinate system may be provided for the radiotherapy system 100 to define a location of a component (e.g., an absolute location, a location relative to another component) and/or a movement of the component. For illustration purposes, a coordinate system 401 is provided in FIG. 4. The coordinate system 401 may be a right-handed Cartesian system including an X-axis, a Y-axis, and a Z-axis. The X-Y plane shown in FIG. 4 may be perpendicular to the first direction, and the Z-axis may be parallel to the first direction. The origin of the coordinate system 401 may be located at an isocenter of the radiotherapy device 110 (e.g., a rotation center of the radiation source SO). In some embodiments, the origin of the coordinate system 401 may be located at any other location relating to the radiotherapy device 110, e.g., a location of the radiation source SO.

In some embodiments, the beam-limiting device may include a plurality of movable components (e.g., a plurality of leaves 410) arranged on the end surface of the beam-limiting device. The end surface may be perpendicular to the first direction and also referred to as a first plane. Each of the plurality of leaves 410 may be movable along the first direction and/or a second direction in the first plane. The second direction may be perpendicular to the first direction. For example, a leaf 410 may move along the first direction to adjust the distance between the beam-limiting device and the subject 400. As another example, a leaf 410 may move along a second direction in the first plane to adjust the shape and/or size of a radiation field of the beam-limiting device. The movement of the leaf 410 in the first plane may also be referred to as an open-close movement. The first plane may be movable with the movement of the beam-limiting device along the first direction.

In some embodiments, the resolution and/or the conformity of the beam-limiting device may be adjusted by moving the leaves 410. For example, when the leaves 410 of the beam-limiting device move along the first direction towards the subject 400, the resolution of the beam-limiting device may be improved. As another example, when the leaves 410 of the beam-limiting device move in the first plane, the shape of the radiation field of the beam-limiting device may be adjusted so as to adjust the conformity of the beam-limiting device. As used herein, the conformity of the beam-limiting device may reflect a degree of how the radiation beam passing through the radiation field of the beam-limiting device conforms to a planning region of the subject 400 to be irradiated. For example, the conformity of the beam-limiting device may be measured by a similarity degree between an irradiation region of the subject 400 and the planning region. An irradiation region of a subject refers to a region irradiated or predicted to be irritated by a radiation beam emitted by a radiation source and passing through a radiation field of a beam-limiting device, which is also referred to as an irradiation region of the radiation beam passing through the beam-limiting device. The resolution of the beam-limiting device refers to a boundary accuracy of the irradiation region of the subject 400 formed/projected by the radiation beam passing through the radiation field of the beam-limiting device. A boundary accuracy of an irradiation region of the subject 400 refers to a similarity degree between a boundary of the irradiation region and a boundary of a planning region 420 of the subject 400. If the radiation field remains unchanged, increasing the count (or number) of the plurality of leaves 410 may improve the boundary accuracy of the formed irradiation area and the resolution of the beam-limiting device. If the count (or number) of the plurality of leaves 410 remains unchanged, moving the beam-limiting device toward the subject 400 may improve the resolution of the beam-limiting device.

In some embodiments, the radiation beam emitted from the radiation source SO may have a cone-shape as shown in FIG. 4. When the movable components of the beam-limiting device move along a single direction (such as, the first direction or a second direction in the first plane) during a time period, the shape of the radiation field of the beam-limiting device may vary, and the shape of the irradiation region of the subject 400 may vary and not conform to the planning region of the subject 400 during the time period. For example, when the leaves 410 of the beam-limiting device only move along the first direction, the shape of the irradiation region of the subject 400 may be changed and different from the shape of the planning region of the subject 400, which may result in a change in a radiation dose of the subject 400 and a need of adjusting a treatment plan of the subject 400. Similarly, when the beam-limiting device only moves along a second direction in the first plane, the shape of the irradiation region of the subject 400 may be changed and different from the shape of the planning region of the subject 400, which may result in a change in the radiation dose and a need of changing the treatment plan of the subject 400. Once the treatment plan is adjusted, the radiotherapy device 110 may need to perform a quality assurance (QA) process, which is time-consuming, increases the workload of a user, and reduce the treatment efficiency. As used herein, a QA process refers to a process for the radiotherapy device to perform a simulated treatment without the subject according to the treatment plan before the actual treatment of the subject. The QA process may be used to examine an operating condition of the radiotherapy device. The QA process may also be used to determine of current locations (or initial locations) of the plurality of movable components of the beam-limiting device, based on which a set of target locations of the plurality of movable components of the beam-limiting device during the actual treatment may be determined.

In some embodiments, the leaves 410 of the beam-limiting device may be caused to move along the first direction and in the first plane simultaneously to make the irradiation region of the subject 400 remains changed. For example, the movement of the leaves 410 along the first direction and in the first plane may be determined based on the planning region, so that the irradiation region of the subject 400 may always have the same (or substantially same) shape as the planning region of the subject 400 during the movement of the leaves 410. In this way, there is no need to adjust the treatment plan.

In some embodiments, a leaf 410 may have a compound movement when it moves along the first direction and the second direction in the first plane simultaneously. For example, the leaf 410 may move along a compound direction of the first direction and the second direction. In some embodiments, the compound direction may be coincident with a beam direction corresponding to the leaf 410. As used herein, a beam direction corresponding to a movable component of a beam-limiting device refers to a direction parallel to a radioactive ray in the radiation beam emitted by the radiation source SO that passes through the movable component. For example, the beam direction may be parallel to a generatrix of the cone shape, e.g., a direction OC or OD as shown in FIG. 4. The beam direction corresponding to the leaf 410 on the left of FIG. 4 may be the direction OC as shown in FIG. 4. The beam direction corresponding to the leaf 410 on the right of FIG. 4 may be the direction OD as shown in FIG. 4.

In some embodiments, for each of the plurality of leaves 410, a moving route (e.g., a moving route along the direction OC or OD as shown in FIG. 4) of the leaf 410 may be determined. When the leaves 410 move along their corresponding moving routes, the shape and size of the irradiation region of the subject 400 may remain unchanged or substantially unchanged during the movement. As used herein, the shape of the irradiation region of the subject 400 may be regarded as remaining substantially unchanged if the variation of the shape of the irradiation region of the subject 400 is below a threshold during the movement of the leaves 410. More descriptions regarding the movement and/or the states of the beam-limiting device may be found elsewhere in the present disclosure (e.g., FIG. 7 and the descriptions thereof).

Figure 5:
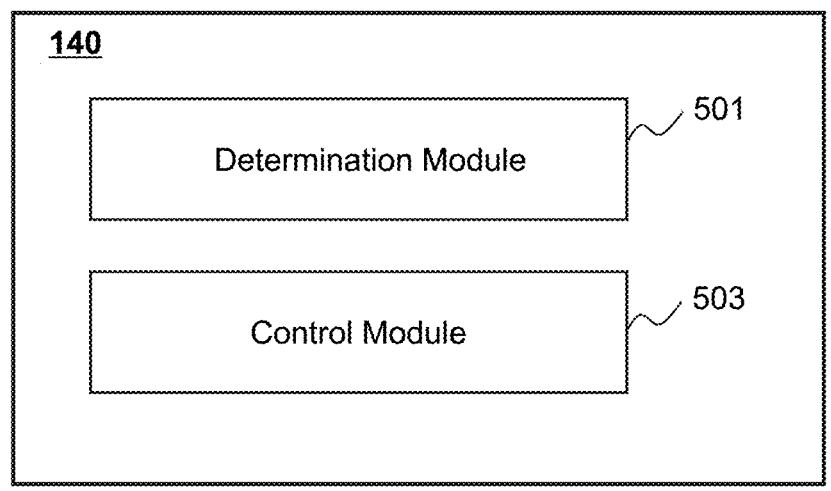
FIG. 5 is a block diagram illustrating an exemplary processing device according to some embodiments of the present disclosure.

FIG. 5 is a schematic diagram illustrating an exemplary processing device according to some embodiments of the present disclosure. As shown in FIG. 5, the processing device 140 may include a determination module 501 and a control module 503.

The determination module 501 may be configured to determine a target location of a beam-limiting device. In some embodiments, the determination module 501 may determine a set of target locations of a plurality of movable components of the beam-limiting device. For example, the determination module 501 may determine the set of target locations based on a treatment plane of a subject to be irradiated by a radiation beam passing through the beam-limiting device. As another example, the determination module 501 may determine the set of target locations based on initial locations of the plurality of movable components and/or a planning region of the subject according to a principle of similar triangles. In some embodiments, the determination module 501 may determine moving routes of the plurality of movable components based on the set of target locations. More descriptions regarding the determination of the set of target locations and the moving routes may be found elsewhere in the present disclosure (e.g., operation 610 in FIG. 6 and operations 701-705 and the descriptions thereof.

The control module 503 may be configured to control a movement of the beam-limiting device. For example, the control module 503 may cause the beam-limiting device to move from a current location (e.g., a system default location) of the beam-limiting device to an initial location of the beam-limiting device. When the beam-limiting device is located at the initial location, an irradiation region of the subject may be the same or substantially same as a planning region of the subject. As another example, the control module 503 may cause the beam-limiting device to move from the initial location of the beam-limiting device to a target location of the beam-limiting device. For instance, the control module 503 may cause the plurality of movable components to move along their moving routes. During the movement of the beam-limiting device from the initial location to the target location, an irradiation region of the subject may remain unchanged or substantially unchanged. More descriptions regarding the control of the movement of the beam-limiting device may be found elsewhere in the present disclosure (e.g., operation 630 in FIG. 6, operation 707 in FIG. 7 and the descriptions thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

Figure 6:
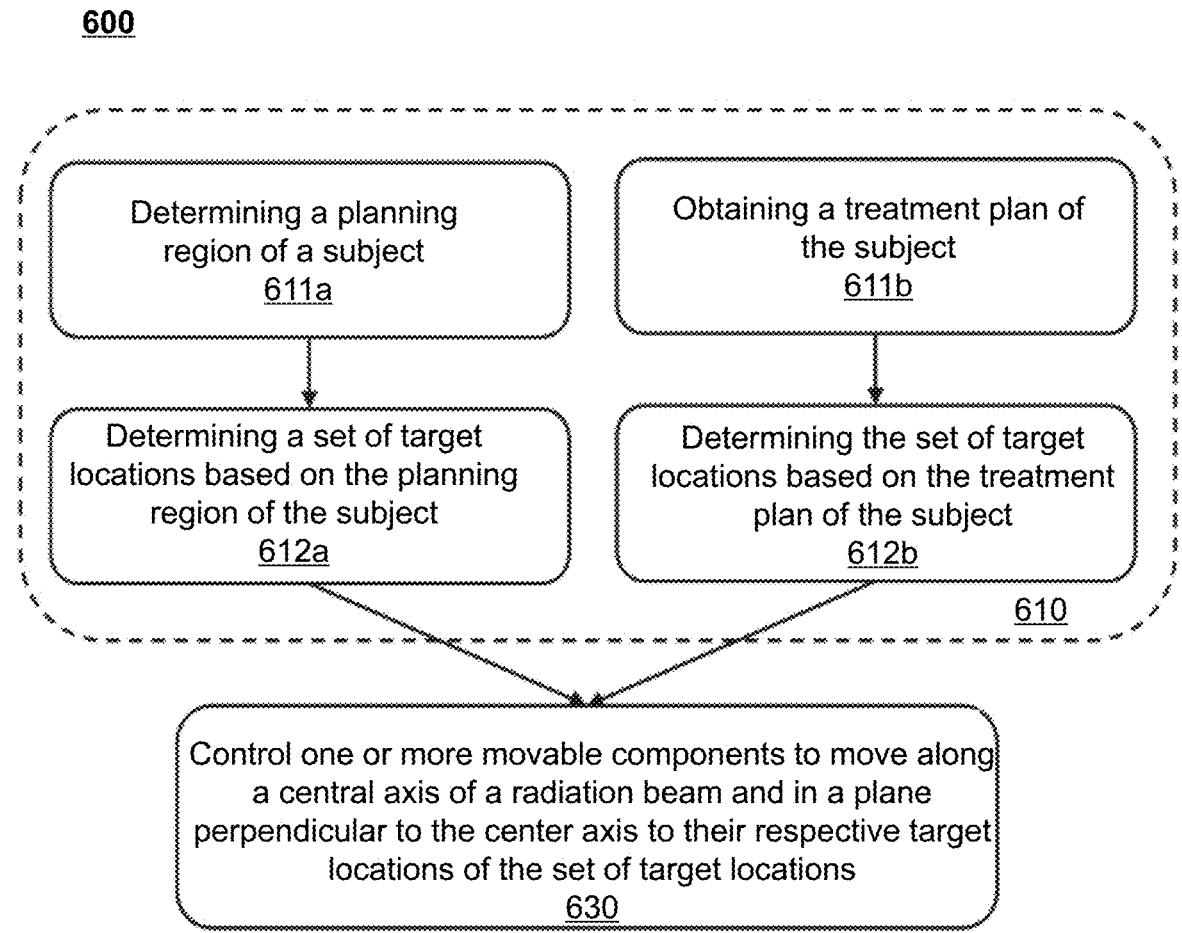
FIG. 6 is a flowchart illustrating an exemplary process for controlling a beam-limiting device according to some embodiments of the present disclosure.

FIG. 6 is a flowchart illustrating an exemplary process for controlling a beam-limiting device according to some embodiments of the present disclosure. In some embodiments, process 600 may be implemented as a set of instructions (e.g., an application) stored in a storage device (e.g., the storage device 130, the storage device 220, and/or the storage 390). The processing device 140 (e.g., the processor 210, the CPU 340, and/or one or more modules illustrated in FIG. 5) may execute the set of instructions, and when executing the instructions, the processing device 140 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. For illustration purposes, the following descriptions are described with reference to the control of a beam-limiting device of the radiotherapy device 110 as described in connection with FIG. 1, and not intended to limit the scope of the present disclosure.

Normally, during a radiation treatment (e.g., a photon treatment, an electron treatment, or a proton treatment), a subject to be radiated may be placed on a couch and radiated by the radiotherapy device 110 from one or more gantry angles. When a gantry of the radiotherapy device 110 rotates to a gantry angle, the beam-limiting device of the radiotherapy device 110 may need to be adjusted such that an irradiation region of the subject may match a planning region of the subject corresponding to the gantry angle. The planning regions of the subject corresponding to different gantry angles may be the same or different. For example, the beam-limiting device may include a plurality of movable components, and a target location of each movable component may need to be determined by performing the process 600.

In some embodiments, the adjustment of the beam-limiting device may be performed before the radiotherapy device 110 emits the radiation beam. In such cases, unless otherwise stated, the term "radiation beam" described hereinafter refers to a radiation beam assumed to be emitted by the radiotherapy device 110, and the term "irradiation region of the subject" described hereinafter refers to an irradiation region of the subject assumed or predicted to be irradiated by the radiation beam passing through the beam-limiting device. Alternatively, the adjustment of the beam-limiting device may be performed when the radiotherapy device 110 is emitting the radiation beam. In such cases, the term "radiation beam" refers to a radiation beam that is being emitted by the radiotherapy device 110, and the term "irradiation region of the subject" refers to an irradiation region of the subject that is radiated by the radiation beam passing through the beam-limiting device.

In 610, the processing device 140 (e.g., the determination module 501) may determine the set of target locations of the movable components of the beam-limiting device when the gantry rotates to a specific gantry angle.

In some embodiments, when the movable components are located at their respective target locations, a radiation beam emitted from a radiation source (e.g., the radiation source SO) may pass through a radiation field of the beam-limiting device formed by the beam-limiting device to irradiate the planning region of the subject. The shape of an irradiation region of the subject may conform to (e.g., be the same or substantially the same as) the shape of the planning region of the subject and the beam-limiting device may have a relatively high conformity at the target location. Additionally or alternatively, during the movement of the movable components to their respective target locations, the shape of the irradiation region of the subject may remain unchanged or substantially unchanged.

In some embodiments, a target location of a movable component may include a first target location along a first direction (e.g., a direction parallel to a center axis of the radiation beam emitted from the radiation source (e.g., the Z-axis direction as shown in FIG. 4)) and a second target location on a second plane (e.g., a plane perpendicular to the center axis (e.g., the X-Y plane as shown in FIG. 4)).

In some embodiments, the first target location of the movable component may be represented as the height of the movable component along the first direction, such as a distance between the movable component and the subject (or the coach) along the first direction. In some embodiments, the movable components of the beam-limiting device may be located on a same end surface (e.g., the first plane) of the beam-limiting device perpendicular to the first direction. The distance between different movable components and the subject (or the coach) may be the same, which may be equal to, for example, a distance between the end surface of the beam-limiting device and a coronal surface of the subject. Additionally or alternatively, the first target location may be represented by a first coordinate of the movable component along the first direction (e.g., a coordinate of the leaf 410 along the Z-axis of the coordinate system 401).

The second target location of the movable component may be represented by, for example, a second coordinate of the movable component on the first plane (e.g., a coordinate of the leaf 410 on the X-Y plane of the coordinate system 401). In some embodiments, the target location of the movable component may be represented by a 3D coordinate in the coordinate system 401, which may include the first coordinate and the second coordinate.

In some embodiments, the processing device 140 may determine the set of target locations based on the planning region of the subject according to the following operations 611a and 612a.

In 611a, the processing device 140 (e.g., the determination module 501) may determine the planning region of the subject (i.e., a region of the subject planned to be radiated).

For example, the processing device 140 may determine the planning region of the subject based on a treatment plan of the subject. As another example, a user (e.g., a doctor or an operator) may input information (e.g., contour information, location information) of the planning region of the subject via a terminal device (e.g., the terminal device 130). The processing device 140 may receive the information of the planning region from the terminal device and determine the planning region. As yet another example, the processing device 140 may obtain a medical image relating to the subject acquired before the treatment. The processing device 140 may identify a lesion in the medical image, and determine the planning region based on the identified lesion.

In 612*a*, the processing device 140 (e.g., the determination module 501) may determine the set of target locations based on the planning region of the subject.

In some embodiments, for each of the plurality of movable components, the processing device 140 may determine an initial location of the movable component. As used herein, an initial location of a movable component refers to a location of the movable component before the movement of the movable component to its target location. When the movable components are at their initial locations, the shape of an initial irradiation region of the subject corresponding to an initial radiation field formed by the movable components at the initial locations may be the same or substantially same as the planning region of the subject. For example, the initial location of the movable component may be a default location set by the radiotherapy system 100. When the gantry rotates to a gantry angle, the movable component may be located at the default location and the irradiation region of the subject may be the same or substantially the same as the planning region of the subject. As another example, the initial location may be an adjusted location adjusted from a current location of the movable component. The adjusted location may be determined by adjusting the current location automatically or manually by a user. For instance, the movable component may be caused to move in the end surface of the beam-limiting device from the current location to the adjusted location such that the initial irradiation region of the subject may be the same or substantially the same as the planning region of the subject. Alternatively, when the movable component is located at the current location, the irradiation region of the subject may be the same or substantially the same as the planning region of the subject. In such cases, the initial location may be the current location of the movable component.

The processing device 140 may then determine the target location of the movable component based on the initial location of the movable component and the planning region of the subject. For example, the processing device 140 may determine the target location of the movable component according to a principle of similar triangles. As another example, the processing device 140 may determine the target location of the movable component based on a preset resolution of the beam-limiting device. For instance, the processing device 140 may determine the set of target locations such that a resolution of the beam-limiting device is greater than the preset resolution. More descriptions regarding the determination of the set of target locations based on the planning region of the subject may be found elsewhere in the present disclosure (e.g., FIG. 7 and the description thereof).

In some embodiments, the processing device 140 may determine the set of target locations based on the treatment plan of the subject according to the following operations 611*b* and 612*b*.

In 611*b*, the processing device 140 (e.g., the determination module 501) may obtain the treatment plan of the subject.

In some embodiments, the treatment plan may include information that describes how the treatment is planned to be delivered, such as radiation dose information, the information of the planning region of the subject, location information of the beam-limiting device, or the like, or any combination thereof. The radiation dose information may include, for example, a radiation intensity, a radiation duration, a type, etc., of the radiation beam emitted by the radiation source. The information of the planning region of the subject may include a shape, a size, etc., of the planning region. The location information of the beam-limiting device may include a current location of the beam-limiting device (e.g., a location of the beam-limiting device before the treatment). For example, the current location of the beam-limiting device may include a current height of the beam-limiting device, a current location of each of the plurality of movable components (e.g., a current location of a leaf 410). In some embodiments, the location information of the beam-limiting device may include the initial location of the beam-limiting device and/or the target location of the beam-limiting device. The target location of the beam-limiting device may include the set of target locations of the movable components. In some embodiments, the treatment plan may be generated to make the planning region of the subject receive a target radiation dose during the treatment.

In 612*b*, the processing device 140 (e.g., the determination module 501) may determine the set of target locations based on the treatment plan.

In some embodiments, the set of target locations may be pre-determined and stored in the treatment plan. The processing device 140 may directly obtain the set of target locations from the treatment plan. In some embodiments, the processing device 140 may obtain initial locations of the plurality of movable components from the treatment plan. The processing device 140 may further determine the set of target locations based on the initial locations (e.g., according to the principle of similar triangles), which is similar to that described in operation 612*a*.

In 630, the processing device 140 (e.g., the control module 403) may control one or more of the movable components to move to their respective target locations of the set of target locations.

For example, a movable component may be caused to move along the central axis of the radiation beam and in the plane perpendicular to the center axis simultaneously (i.e., move along the first direction and in the first plane) to reach its target location. In other words, the movable component may be controlled to have a compound movement along different directions (i.e., the first direction and a second direction in the first plane), which can improve the efficiency of the movement of the beam-limiting device. In some embodiments, all of the plurality of movable components or a portion of the plurality of movable components may be caused to move. During the movement of the movable components (or a portion thereof), the irradiation region of the subject may remain unchanged or substantially unchanged.

In some embodiments, for each movable component, the processing device 140 may determine a moving route of the movable component based on the initial location and the target location of the movable component. The processing device 140 may cause the movable component to move along its moving route. For example, the processing device 140 may determine the moving route of the movable component by connecting the initial location and the target location. A moving direction of the movable component may be from the initial location to the target location and parallel to the moving route. More descriptions regarding the determination of the moving route may be found elsewhere in the present disclosure (e.g., operation 705 and the description thereof).

In some embodiments, after the subject is irradiated under the specific gantry angle, the subject may need to be irradiated under a next gantry angle. The processing device 140 may cause the gantry to rotate from the specific gantry angle to the next gantry angle. The beam-limiting device and the radiation source may be rotated with the gantry from the specific gantry angle to the next gantry angle. The process 600 may be performed for the next gantry angle. For example, for each of the plurality of movable components, the processing device 140 may determine a second initial location and a second target location of the movable component corresponding to the next gantry angle. The processing device 140 may determine a plurality of second moving routes of the plurality of movable components corresponding to the next gantry angle. The processing device 140 may cause the plurality of movable components to move along their respective second moving routes corresponding to the next gantry angle. During the movement of the movable components along their respective second moving routes, the shape of a second irradiation region of the radiation beam passing through the beam-limiting device remains unchanged or substantially unchanged. For example, the shape of the second irradiation region of the subject may be the same or substantially the same as a planning region of the subject corresponding to the next gantry angle. The planning region corresponding to the next gantry angle may be the same as or different from the planning region corresponding to the specific gantry angle. More description regarding the movement of the plurality of movable components under different gantry angles may be found elsewhere in the present disclosure (e.g., FIG. 8 and the description thereof).

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 600. For example, a storing operation may be added elsewhere in the process 600. In the storing operation, the processing device 140 may store information and/or data (e.g., the set of target locations) used or obtained in operations of the process 600 in a storage device (e.g., the storage device 130) disclosed elsewhere in the present disclosure. In some embodiments, one or more operations of the process 600 may be omitted. For example, operation 612b may be omitted. After operation 611a, the process 600 may directly proceed to operation 630.

Figure 7:
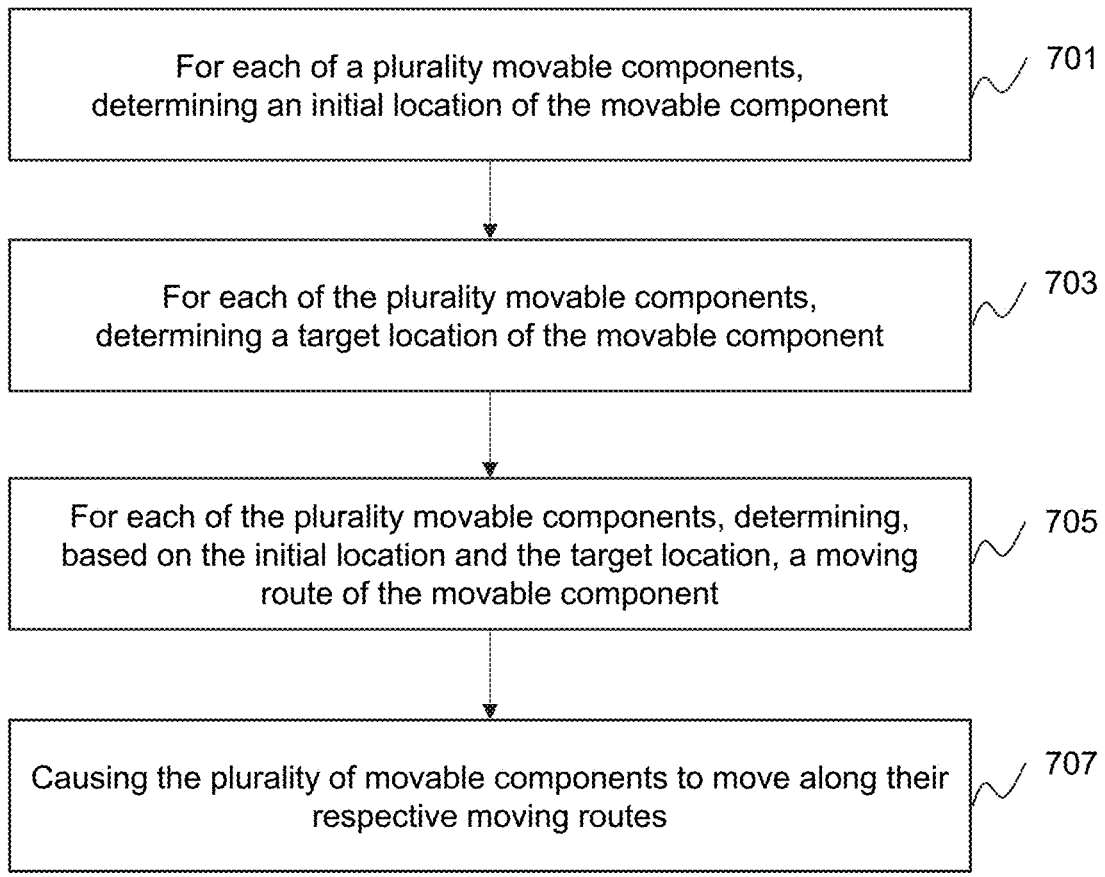
FIG. 7 is a flowchart illustrating an exemplary process for adjusting a beam-limiting device including a plurality of movable components according to some embodiments of the present disclosure.

FIG. 7 is a flowchart illustrating an exemplary process for adjusting a beam-limiting device including a plurality of movable components according to some embodiments of the present disclosure. In some embodiments, process 700 may be implemented as a set of instructions (e.g., an application) stored in a storage device (e.g., the storage device 130, storage device 220, and/or storage 390). The processing device 140 (e.g., the processor 210, the CPU 340, and/or one or more modules illustrated in FIG. 5) may execute the set of instructions, and when executing the instructions, the processing device 140 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In some embodiments, one or more operations in the process 600 may be achieved by the implementation of the process 700. For illustration purposes, the following descriptions are described with reference to the implementation of the process 700 when a gantry of a radiotherapy device remains at a specific gantry angle. When the gantry remains at the specific gantry angle, the beam-limiting device may be configured to irradiate a planning region of the subject corresponding to the specific gantry angle.

In 701, for each of the plurality of movable components, the processing device 140 (e.g., the determination module 501) may determine an initial location of the movable component.

In some embodiments, the initial location may include a first initial location along the first direction and a second initial location in the first plane. As described in 612a, the initial location of the movable component may be a default location, an adjusted location, or a current location of the movable component.

For example, if the initial location is a default location, the default location may be previously determined and stored in, for example, a treatment plan of the subject. The processing device 140 may obtain the treatment plan and determine the initial location of the movable component based on the treatment plan. When the plurality of movable components are at their corresponding initial locations, the plurality of movable components may form an initial radiation field of the beam-limiting device and an initial irradiation region of the subject corresponding to the initial radiation field may be the same as or substantially the same as the planning region of the subject. For example, a similarity degree between the initial irradiation region of the subject and the planning region of the subject may greater than or equal to a similarity threshold. The similarity degree between two regions may be measured by, for example, a ratio of the area of an overlapped region of the two regions to the area of one of the two regions, a ratio of the area of one of the two regions to the area of another one of the two regions, etc.

As another example, if the initial location is an adjusted location, the processing device 140 may determine a current location of the movable component. For example, after the gantry rotates to the specific gantry angle, the beam-limiting device may be located at a preset location before the treatment is applied to the subject (e.g., before the radiation field of the beam-limiting device is open). The preset location may be stored in a storage device as described in the present disclosure (e.g., as factory setting information of the beam-limiting device, or the treatment plan of the subject). If the beam-limiting device does not move after the gantry rotates to the specific gantry angle, the preset location of the beam-limiting device may be determined as the current location of the beam-limiting device. The current location of the beam-limiting device may include a current location of each of the plurality of movable components, such as a first current location (e.g., a current height) along the first direction and a second current location in the first plane. Taking the specific movable component as an example, the processing device 140 may determine the current location of the movable component based on the preset location of the beam-limiting device obtained from the storage device. Alternatively, the processing device 140 may determine the current location of the movable component based on, for example, a user input relating to the current location or location information detected by a location sensor of the beam-limiting device.

Further, the processing device 140 may determine the initial location of the movable component based on the current location. For example, if the irradiation region of the subject is the same or substantially same as the planning region, the current location of the movable component may be determined as the initial location of the movable component. Alternatively, the processing device 140 may determine the initial location based on the current location of the movable component and the planning region of the subject. The first initial location of the initial location along the first direction may be the same as the first current location of the current location along the first direction, i.e., the initial location includes a same height as the current location. The second initial location of the initial location in the first plane may be determined based on the planning region according to a principle of similar triangles, which will be described in operation 703. For example, the processing device 140 may determine the second initial locations of the plurality of movable components, such that a second initial irradiation region of the subject corresponding to a second initial radiation field formed by the movable components at the second initial locations may match the planning region. The processing device 140 may further cause the movable components to move from their corresponding current locations to their corresponding initial locations.

In 703, for each of the plurality of movable components, the processing device 140 (e.g., the determination module 501) may determine a target location of the movable component.

In some embodiments, when the plurality of movable components are located at their corresponding target locations, the plurality of movable components may form a target radiation field of the beam-limiting device, and the shape of a target irradiation region of the subject corresponding to the target radiation field of the beam-limiting device may be the same as or substantially the same as the initial irradiation region of the subject. For example, the similarity degree between the target irradiation region and the initial irradiation region of the subject may be greater than or equal to the similarity threshold.

Additionally or alternatively, a conformity degree of the target irradiation region with respect to the planning region of the subject may be greater than or equal to a threshold conformity degree (e.g., 100%, 80%, etc.). The conformity degree of the target irradiation region to the planning region may be measured by, for example, a ratio of the area of the target irradiation region to the area the planning region, a ratio of the area of an overlapped region between the target irradiation region and the planning region to the area of the planning region. For example, if the conformity degree is equal to 100%, the target irradiation region of the subject may be the same as the planning region of the subject. If the conformity degree is equal to 80%, the ratio of the area of the target irradiation region of the subject to the area the planning region of the subject may be equal to 80%. In some embodiments, when the plurality of movable components are located at their corresponding target locations, the beam-limiting device may have a target resolution, which is greater than an initial resolution of the beam-limiting device when the plurality of movable components are located at their corresponding initial locations.

In some embodiments, the processing device 140 may determine the target locations of the movable components based on the treatment plan by, for example, performing operation 612b as described in connection with FIG. 6. Alternatively, the processing device 140 may determine the target locations based on the initial locations of the movable components according to the principle of similar triangles. For example, referring to FIG. 4, two states (e.g., a first state and a second state) of the beam-limiting device including a plurality of leaves 410 are provided. A distance between the radiation source SO to the subject 400 may be denoted as LC. A distance between the beam-limiting device and the radiation source SO may be denoted by $LM_1$ when the beam-limiting device is at the first state. A distance between the beam-limiting device and the radiation source SO may be denoted by $LM_2$ when the beam-limiting device is at the second state.

When the beam-limiting device is at the first state, the plurality of leaves 410 are located at their corresponding initial locations. The distance between the leaves 410 and the subject along the first direction may be equal to (LC-$LM_1$), and the plurality of leaves 410 may form an initial radiation field having a first diameter denoted by $DM_1$. A radiation beam passing through the initial radiation field may irradiate on an initial radiated region of the subject 400.

When the beam-limiting device is at the second state, the plurality of leaves 410 are at their corresponding target locations. The distance between the leaves 410 and the subject along the first direction may be equal to (LC-$LM_2$) and the plurality of leaves 410 may form a target radiation field having a second diameter denoted by $DM_2$. A radiation beam passing through the target radiation field may form a target irradiation region of the subject. It is desired that the initial radiated region and the target irradiation region conform to the planning region 420 of the subject 400. For example, if the planning region 420 has a length DC along the X-axis direction of the coordinate system 401, both the initial radiated region and the target irradiation region may also have the length DC along the X-axis direction as shown in FIG. 4. A first triangle denoted by SO-$DM_1$, a second triangle denoted by SO-$DM_2$ and/or a third triangle denoted by SO-DC may be similar triangles. The initial radiated region of the subject 400 may conform to the planning region 420 of the subject 400 if Equation (1) as below is satisfied:

$$DM_1 = \frac{LM_1}{LC} \times DC. \qquad (1)$$

A triangle denoted by SO-$DM_2$ may need to be a similar triangle to a triangle denoted by SO-$DM_1$ to make the target irradiation region of the subject 400 corresponding to the target locations of the leaves 410 conform to the planning region 420. The processing device 140 may determine the target locations of the leaves 410 based on $DM_1$ and $LM_1$ according to the principle of similar triangles. For example, $LM_2$ may be equal to any value greater than $LM_1$ and smaller than a difference between LC and a minimum distance between the beam-limiting device and the subject 400. The beam-limiting device may be too close to the subject (e.g., collide with the subject) if the distance between the beam-limiting device and the subject is smaller than the minimum distance. $DM_2$ may be determined according to Equation (2) as below:

$$DM_2 = \frac{LM_2}{LM_1} \times DM_1. \quad (2)$$

In some embodiments, the processing device 140 may randomly determine $LM_2$, determine $DM_2$ according to Equation (2), and determine the target locations of the leaves 410 based on $LM_2$ and $DM_2$. For example, a coordinate of a leaf 410 along the Z-axis direction may be determined based on $LM_2$, and a coordinate of the leaf 410 on the X-Y plane may be determined based on $DM_2$. In some embodiments, a triangle denoted by SO-$DM_2$ may need to be a similar triangle to a triangle denoted by SO-DC such that the target irradiation region of the subject 400 corresponding to the target locations of the leaves 410 conforms to the planning region 420. The processing device 140 may determine the $DM_2$ according to Equation (3) as below:

$$DM_2 = \frac{LM_2}{LC} \times DC. \quad (3)$$

In some embodiments, the processing device 140 may determine a plurality of values of $LM_2$, and determine a set of candidate target locations of the plurality of leaves 410 for each value of $LM_2$. Then, the processing device 140 may determine a set of target locations from a plurality of sets of candidate target locations. For example, for each of the sets of candidate target locations, the processing device 140 may determine a resolution of the beam-limiting device when the plurality of movable components are located at their corresponding candidate target location of the set of candidate target locations. The processing device 140 may determine a maximum candidate resolution from the plurality of candidate resolutions corresponding to the plurality of sets of candidate target locations. The processing device 140 may designate the set of candidate target locations corresponding to the maximum candidate resolution as the set of target locations.

In some embodiments, the processing device 140 may determine a resolution corresponding to a set of candidate target locations by determining a full width at half maximum (FWHM) of the beam-limiting device. The FWHM may reflect a penumbra effect of the candidate irradiation region of the subject corresponding to the set of candidate target location. For example, the FWHM may be determined according to Equation (4) as follows:

$$FWHM = \frac{D}{L}(z_0 + L), \quad (4)$$

where D denotes a diameter of the candidate radiation field of the beam-limiting device corresponding to the set of candidate target locations, L denotes a thickness of the beam-limiting device, and $z_0$ denotes a distance between the subject and the beam-limiting device. In some embodiments, the greater the FWHM of the beam-limiting device is, the higher the resolution of the beam-limiting device corresponding to the set of candidate target locations may be. The greater the D is or the smaller the $z_0$ is, the higher the resolution may be. In some embodiments, the D may be less than or equal to a diameter of a maximum radiation field that the beam-limiting device can achieve. The $z_0$ may be greater than or equal to the minimum distance as aforementioned between the beam-limiting device and the subject.

In 705, for each of the plurality of movable components, the processing device 140 (e.g., the determination module 501) may determine, based on the initial location and the target location, a moving route of the movable component.

For example, the moving route of a movable component may be defined by, for example, an initial location, a target location, a moving direction, a moving speed, or the like, or any combination thereof, of the movable component. In some embodiments, the moving route of the movable component may include a single moving route connecting the initial location and the target location of the movable component. Alternatively, the moving route of the movable component may include a first moving route along the first direction and a second moving route in the first plane. The single moving route may be regarded as a compound route of the first moving route and the second moving route.

In some embodiments, the moving route of the movable component may be parallel to a beam direction corresponding to the movable component. For example, referring to FIG. 4, the moving route of the left leaf 410 may be parallel to the direction OC, and the moving route of the right leaf 410 may be parallel to the direction OD. When the left leaf 410 moves along the direction OC and the right leaf 410 moves along the direction OD simultaneously with a same speed, an irradiation region of the subject 400 may be unchanged or substantially unchanged because a triangle constructed by the radiation source SO and any two points with a same height on the direction OC and the direction OD may be a similar triangle as the triangle denoted by SO-$DM_1$.

In some embodiments, as aforementioned, the initial location of a leaf 410 may include a first initial location along the first direction and a second initial location in the first plane, and the target location of the leaf 410 may include a first target location along the first direction and a second target location in the first plane. The processing device 140 may determine one or more moving parameters (e.g., a constant speed or an acceleration) for the leaf 410 so that the leaf 410 can reach the first target location and the second target location at a same or substantially same time point. For example, the distance that needs to be traversed by the leaf 410 along the first direction may be equal to ($LM_2$-$LM_1$), and the distance that needs to be traversed by the leaf 410 in the first plane may be equal to $$\frac{DM2 - DM1}{2}.$$

If the leaf 410 moves uniformly, e.g., at a constant speed, a ratio of a first speed of the leaf 410 along the first direction and a second speed of the leaf 410 in the first plane may be equal to $$\frac{LM2 - LM1}{2(DM2 - DM1)}.$$

Alternatively, the leaf 410 may be caused to move at a compound speed of the first speed and the second speed along a beam direction. As another example, if the leaf 410 moves un-uniformly, e.g., with an acceleration, a ratio of a first acceleration of the leaf 410 along the first direction and a second acceleration of the leaf 410 in the first plane may be equal to $$\frac{LM2 - LM1}{2(DM2 - DM1)}.$$

Alternatively, the leaf 410 may be caused to move with a compound acceleration of the first acceleration and the second acceleration along a beam direction. In some embodiments, the plurality of movable components may be caused to reach their corresponding target locations at a same or substantially same time point. Referring to FIG. 4, the left leaf 410 and the right leaf 410 may be caused to reach their target locations corresponding to the second state at a same or substantially same time.

In 707, the processing device 140 (e.g., the control module 503) may cause the plurality of movable components to move along their respective moving routes.

During the movement of the plurality of movable components, the shape and size of an irradiation region of the subject may be unchanged or substantially unchanged. Additionally or alternatively, the irradiation region may be the same or substantially the same as that of the planning region of the subject. In this way, during the movement of the beam-limiting device, a radiation dose received by the subject may remain unchanged and keep consistent with the treatment plan of the subject. Furthermore, when the plurality of movable components are at their respective target locations, the beam-limiting device may have better conformity and higher resolution than the plurality of movable components are at their respective initial locations, which may improve the treatment accuracy.

Additionally, in some embodiments, the processing device 140 may cause the plurality of movable components to move from the first state to the second state along the first direction and a second direction in the first plane simultaneously, which avoids adjusting the beam-limiting device in each direction successively and improves the moving efficiency of the beam-limiting device.

In some embodiments, the irradiation region may be formed by one or more actuated movable components of the plurality of movable components. That is, the one or more actuated movable components may form a radiation field, and a radiation beam may pass through the radiation field to form the irradiation region. As used herein, when a movable component (e.g., the leaf 410 on the left shown in FIG. 4) is not actuated (also referred to as the movable component is closed), a distance between the movable component and its adjacent movable component (e.g., the leaf 410 on the right in FIG. 4 opposite to the leaf 410 on the left) may be less than a preset threshold and the movable component may be not used for shaping; when a movable component is actuated (also referred to as the movable component is closed), the distance between the movable component and its adjacent movable component (e.g., the leaf 410 on the right in FIG. 4 opposite to the leaf 410 on the left) may be greater than the preset threshold and the movable component may be used for shaping. During the movement of the plurality of movable components along their respective moving routes, the number (or count) of the one or more actuated movable components may change (e.g., increase or decrease). Different states of the beam-limiting device may correspond to different counts of the one or more actuated movable components. For example, when the beam-limiting device is at the first state shown in FIG. 4, the beam-limiting device may include a first count of actuated movable components (e.g., actuated leaves) for shaping; when the beam-limiting device is at the second state shown in FIG. 4, the beam-limiting device may include a second count of actuated movable components for shaping. Since the radiation field of the beam-limiting device at the first state is smaller than that of the beam-limiting device at the second state, the second count of actuated components at the second state may be greater than the first count of actuated components at the first state. Accordingly, during the movement of the beam-limiting device from the first state to the second state, the count of the one or more actuated movable components may increase.

It should be noted that the above description regarding process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted in the process 700. For example, a storing operation for storing information/data used and/or generated during the adjustment of the beam-limiting device may be added in the process 700. As another example, operation 701 may be omitted. In some embodiments, operations 705 and 707 may be implemented in a single operation.

Figure 8:
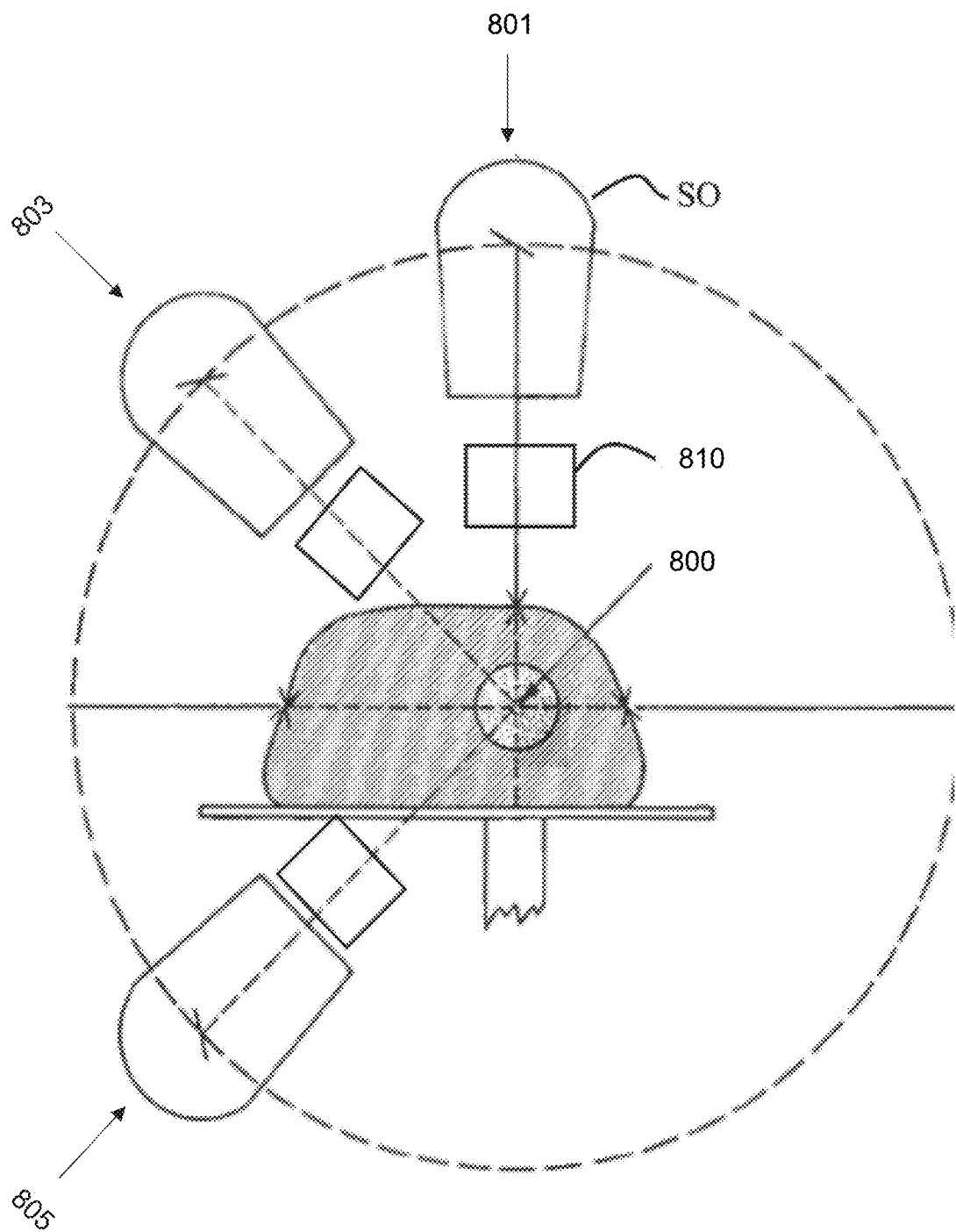
FIG. 8 is a schematic diagram illustrating an exemplary beam-limiting device under different gantry angles according to some embodiments of the present disclosure.

FIG. 8 is a schematic diagram illustrating an exemplary beam-limiting device under different gantry angles according to some embodiments of the present disclosure. As shown in FIG. 8, a radiation source SO and a beam-limiting device 810 may be mounted on a gantry (not shown) that can rotate to different gantry angles. A subject 800 placed on a couch may need to be irradiated by the radiation source SO under different gantry angles (e.g., gantry angles 801, 803, and 805). When the gantry rotates to a specific gantry angle, the radiation source SO may emit a radiation beam from the specific gantry angle, and the radiation beam may pass through a radiation field of the beam-limiting device 810 to irradiate a planning region of the subject corresponding to the specific gantry angle.

The beam-limiting device 810 may need to be adjusted to change its distance to the subject 800 and its radiation field simultaneously to improve the resolution and conformity of the beam-limiting device. For example, when the gantry rotates to a specific gantry angle (e.g., one of the gantry angles 801, 803, and 805), each movable component of the beam-limiting device 810 may be caused to move to an initial location and/or move from the initial location to a target location by performing the process 600 and/or the process 700. An initial radiated region of the subject 800 corresponding to an initial radiation field formed by the movable components of the beam-limiting device 810 at their corresponding initial locations, and a target radiation region of the subject 800 corresponding to a target radiation field formed by the movable components of the beam-limiting device 810 at their corresponding target locations may both match a planning region of the subject 800 corresponding to the specific gantry angle. During the movement of each movable component of the beam-limiting device 810, the shape of an irradiation region of the subject 800 may remain unchanged or substantially unchanged.

In some embodiments, the subject 800 may be treated according to a static treatment plan. According to the static treatment plan, the radiation source SO may not emit radiation beams until the radiation source SO is rotated to a specific gantry angle and the beam-limiting device 810 is moved to a target location corresponding to the specific gantry angle. Merely by way of example, the radiation source SO may emit a radiation beam toward the subject 800 after the gantry rotates to the gantry angle 801 and the beam-limiting device 810 is moved to its target location corresponding to the gantry angle 801. This may reduce the complexity of controlling the movement of the beam limiting device 810 and the difference between a radiation dose received during the treatment by the subject 800 and a planning radiation dose specified in the static treatment plan. In some embodiments, the subject 800 may be treated according to a dynamic treatment plan. According to the dynamic treatment plan, the radiation source SO may keep emitting radiation beams during the whole treatment of the subject 800. In such cases, in the making of the dynamic treatment plan, a radiation dose emitted by the radiation source SO during the movement of the beam-limiting device 810 and the radiation source SO (e.g., the rotation of the gantry to different gantry angles, and/or the movement of the beam-limiting device 810 to different target locations under a specific gantry angle) may need to be taken into consideration, such that the radiation doses received by the subject 800 under different gantry angles may be reasonably allocated and the total radiation dose received by the subject 800 may not exceed or below a desired dose.

Merely by way of example, before the treatment, the radiation source SO and the beam-limiting device 810 may be located at their default locations under the gantry angle 801. The radiation source SO may keep emitting radiation beams during the treatment of the subject 800. Each movable component of the beam-limiting device 810 may be directed to move from its default location under the gantry angle 801 to an initial location L1 corresponding to the gantry angle 801. Then, each movable component of the beam-limiting device 810 may be directed to move from the initial location L1 to a target location T1 corresponding to the gantry angle 801, during which the shape of an irradiation region of the subject 800 may be the same or substantially the same as a planning region corresponding to the gantry angle 801 and remain unchanged or substantially unchanged. After the treatment under the gantry angle 801 is finished, the gantry may rotate from the gantry angle 801 to the gantry angle 803. During the rotation of the gantry, the radiation source SO may be located at an unchanged location with respect to the gantry, and each movable component of the beam-limiting device 810 may be directed to move from the target location T1 to an initial location L2 corresponding to the gantry angle 803. Then, each movable component of the beam-limiting device 810 may be directed to move from the initial location L2 to a target location T2 corresponding to the gantry angle 803, during which the shape of an irradiation region of the subject 800 may be the same or substantially the same as a planning region corresponding to the gantry angle 803 and remain unchanged or substantially unchanged. In such cases, during the delivery of the dynamic treatment plan, the radiation dose received by the subject 800 may remain unchanged or substantially unchanged when each movable component of the beam-limiting device 801 moves from an initial location to a target location under a specific gantry angle. Further, the location of each movable component of the beam-limiting device 810 may be adjusted under different gantry angles to optimize the resolution and/or conformity of the beam-limiting device 810.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for adjusting a beam-limiting device, the beam-limiting device including a plurality of movable components for shaping a radiation beam, the system comprising:
    at least one storage device including a set of instructions; and
    at least one processor configured to communicate with the at least one storage device, wherein when executing the set of instructions, the at least one processor is configured to direct the system to perform operations including:
    for each of the plurality movable components,
        determining an initial location of the movable component;
        determining a target location of the movable component; and
        determining, based on the initial location and the target location, a moving route of the movable component, wherein the movable component moves along a compound direction of a first direction and a second direction, the first direction being parallel to a center axis of the radiation beam emitted from the radiation source, and the second direction being in a plane perpendicular to the first direction; and
    causing the plurality of movable components to move along their respective moving routes, wherein
        during the movement of the plurality of movable components along their respective moving routes, the shape of an irradiation region of the radiation beam passing through the beam-limiting device remains unchanged.

2. The system of claim 1, wherein
    the radiation beam includes a center axis,
    for each of the plurality of movable components, its initial location includes a first initial location along the center axis and a second initial location on a plane perpendicular to the center axis, and its target location includes a third location along the center axis and a fourth location on the plane.

3. The system of claim 1, wherein for each of the plurality of movable components, the determining a target location of the movable component includes:
    determining a region of interest (ROI) planned to be radiated; and
    determining the target location of each of the plurality of movable components based on the ROI and the initial locations of the plurality of movable components such that during the movement of the plurality of movable components, the irradiation region is the same as the ROI.

4. The system of claim 3, wherein the target location of each of the plurality of movable components is determined according to a principle of similar triangles.

5. The system of claim 4, wherein the system further includes a radiation source, a first triangle is similar to a second triangle, the first triangle is formed by the radiation source and a first diameter of an initial radiation field formed by the plurality movable components at their corresponding initial locations, and the second triangle is formed by the radiation source and a second diameter of a target radiation field formed by the plurality movable components at their corresponding target locations.

6. The system of claim 1, wherein the beam-limiting device is mounted on a gantry of a radiotherapy device,
the initial location and the target location of each of the plurality of movable components correspond to a first gantry angle, and
during the movement of the plurality of movable components, the gantry remains at the first gantry angle.

7. The system of claim 6, wherein the at least one processor is further configured to direct the system to perform the operations including:
causing the gantry to rotate from the first gantry angle to a second gantry angle;
for each of the plurality movable components,
determining a second initial location and a second target location of the movable component corresponding to the second gantry angle; and
determining, based on the second initial location and the second target location, a second moving route of the movable component; and
causing the plurality of movable components to move along their respective second moving routes, wherein
during the movement of the plurality of movable components along their respective second moving routes, the shape of a second irradiation region of the radiation beam passing through the beam-limiting device remains unchanged, and the gantry remains at the second gantry angle.

8. The system of claim 1, wherein the beam-limiting device includes a multi-leaf collimator, and the plurality of movable components include a plurality of leaves of the multi-leaf collimator.

9. The system of claim 1, wherein the radiation beam includes at least one of a radioactive beam, a photon beam, or an electron beam.

10. The system of claim 1, wherein
when the plurality of movable components are at their respective initial locations, the beam-limiting device has a first resolution, and
when the plurality of movable components are at their respective target locations, the beam-limiting device has a second resolution that is greater than the first resolution.

11. The system of claim 1, wherein during the movement of the plurality of movable components along their respective moving routes, the size of an irradiation region of the radiation beam passing through the beam-limiting device remains unchanged.

12. The system of claim 1, wherein the irradiation region is formed by one or more actuated movable components of the plurality of movable components, and during the movement of the plurality of movable components along their respective moving routes, a count of the one or more actuated movable components increases.

13. The system of claim 1, wherein the radiation beam is emitted from a radiation source and has a cone-shape, and the compound direction is parallel to a generatrix of the cone-shape.

14. The system of claim 1, wherein the movable component moves along the beam direction of the radiation beam that passes through the irradiation region defined by the plurality of movable components.

15. A method for adjusting a beam-limiting device, the beam-limiting device including a plurality of movable components for shaping a radiation beam, implemented on a computing device including at least one processor and at least one storage device, the method comprising:
for each of the plurality movable components,
determining an initial location of the movable component;
determining a target location of the movable component; and
determining, based on the initial location and the target location, a moving route of the movable component, wherein the movable component moves along a compound direction of a first direction and a second direction, the first direction being parallel to a center axis of the radiation beam emitted from the radiation source, and the second direction being in a plane perpendicular to the first direction; and
causing the plurality of movable components to move along their respective moving routes, wherein
during the movement of the plurality of movable components along their respective moving routes, the shape of an irradiation region of the radiation beam passing through the beam-limiting device remains unchanged.

16. The method of claim 15, wherein
the radiation beam includes a center axis,
for each of the plurality of movable components, its initial location includes a first initial location along the center axis and a second initial location on a plane perpendicular to the center axis, and its target location includes a third location along the center axis and a fourth location on the plane.

17. The method of claim 15, wherein for each of the plurality of movable components, the determining a target location of the movable component includes:
determining a region of interest (ROI) planned to be radiated; and
determining the target location of each of the plurality of movable components based on the ROI and the initial locations of the plurality of movable components such that during the movement of the plurality of movable components, the irradiation region is the same as the ROI.

18. The method of claim 17, wherein the target location of each of the plurality of movable components is determined according to a principle of similar triangles.

19. The method of claim 1, wherein the beam-limiting device is mounted on a gantry of a radiotherapy device,
the initial location and the target location of each of the plurality of movable components correspond to a first gantry angle, and
during the movement of the plurality of movable components, the gantry remains at the first gantry angle.

20. A non-transitory computer readable medium, comprising executable instructions that, when executed by at least one processor, direct the at least one processor to perform a method for adjusting a beam-limiting device, the beam-limiting device including a plurality of movable components for shaping a radiation beam, the method comprising:

for each of the plurality movable components,
   determining an initial location of the movable component;
   determining a target location of the movable component; and
   determining, based on the initial location and the target location, a moving route of the movable component, wherein the movable component moves along a compound direction of a first direction and a second direction, the first direction being parallel to a center axis of the radiation beam emitted from the radiation source, and the second direction being in a plane perpendicular to the first direction; and
causing the plurality of movable components to move along their respective moving routes, wherein
   during the movement of the plurality of movable components along their respective moving routes, the shape of an irradiation region of the radiation beam passing through the beam-limiting device remains unchanged.

* * * * *